(12) United States Patent
Weitzner et al.

(10) Patent No.: US 8,057,462 B2
(45) Date of Patent: Nov. 15, 2011

(54) MEDICAL DEVICE CONTROL SYSTEM

(75) Inventors: Barry Weitzner, Acton, MA (US); John Golden, Norton, MA (US); Richard Rothstein, Etna, NH (US); Anna Chen, Hopatcong, NJ (US); Dan Bacon, Fitchburg, MA (US); Kim Dang, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1191 days.

(21) Appl. No.: 11/474,114

(22) Filed: Jun. 22, 2006

(65) Prior Publication Data

US 2007/0010801 A1 Jan. 11, 2007

Related U.S. Application Data

(63) Continuation-in-part of application No. 11/165,593, filed on Jun. 22, 2005, now Pat. No. 7,618,413.

(51) Int. Cl.
*A61B 17/00* (2006.01)

(52) U.S. Cl. ............................................ 606/1; 600/146

(58) Field of Classification Search .................. 600/101, 600/104, 117, 118, 121, 131, 146, 148, 149; 604/95.04; 606/1
See application file for complete search history.

(56) References Cited

U.S. PATENT DOCUMENTS

| | | | | |
|---|---|---|---|---|
| 5,254,088 A | * | 10/1993 | Lundquist et al. | 604/95.04 |
| 5,284,130 A | * | 2/1994 | Ratliff | 600/229 |
| 5,325,845 A | * | 7/1994 | Adair | 600/114 |
| 6,013,024 A | * | 1/2000 | Mitsuda et al. | 600/146 |
| 6,033,378 A | * | 3/2000 | Lundquist et al. | 604/95.01 |
| 6,551,237 B2 | * | 4/2003 | Matsui | 600/118 |
| 6,793,622 B2 | * | 9/2004 | Konomura et al. | 600/152 |
| 7,338,505 B2 | * | 3/2008 | Belson | 606/150 |
| 7,410,483 B2 | * | 8/2008 | Danitz et al. | 606/1 |
| 7,608,083 B2 | * | 10/2009 | Lee et al. | 606/130 |
| 2002/0165430 A1 | * | 11/2002 | Matsui | 600/118 |
| 2003/0018237 A1 | * | 1/2003 | Okada | 600/146 |
| 2003/0050649 A1 | * | 3/2003 | Brock et al. | 606/130 |
| 2003/0092965 A1 | * | 5/2003 | Konomura et al. | 600/146 |
| 2003/0135204 A1 | * | 7/2003 | Lee et al. | 606/1 |
| 2004/0059191 A1 | * | 3/2004 | Krupa et al. | 600/146 |
| 2004/0181140 A1 | * | 9/2004 | Falwell et al. | 600/374 |
| 2004/0193016 A1 | * | 9/2004 | Root et al. | 600/146 |
| 2004/0236316 A1 | | 11/2004 | Danitz et al. | |
| 2004/0267093 A1 | * | 12/2004 | Miyagi et al. | 600/146 |
| 2005/0075538 A1 | * | 4/2005 | Banik et al. | 600/141 |
| 2005/0096694 A1 | | 5/2005 | Lee | |
| 2005/0154261 A1 | * | 7/2005 | Ohline et al. | 600/141 |
| 2005/0245789 A1 | * | 11/2005 | Smith et al. | 600/159 |
| 2006/0007184 A1 | * | 1/2006 | Rosenberg et al. | 345/173 |

FOREIGN PATENT DOCUMENTS

| | | |
|---|---|---|
| WO | WO 94/21179 A2 | 9/1994 |
| WO | WO 97/12557 A1 | 4/1997 |

\* cited by examiner

*Primary Examiner* — John P Leubecker
*Assistant Examiner* — Christopher Sponheimer
(74) *Attorney, Agent, or Firm* — Finnegan, Henderson, Farabow, Garrett & Dunner, LLP

(57) ABSTRACT

A control system for allowing a user to control the orientation of a medical device or a medical instrument in a variety of directions. An actuator selectively tensions one or more control cables having ends secured at or adjacent a distal tip of the medical device in order to bend the distal tip in a desired direction. In one embodiment, a physician can adjust the movement of the distal tip in a desired direction without affecting the orientation of the medical device in other directions.

20 Claims, 17 Drawing Sheets

MEDICAL DEVICE CONTROL SYSTEM

CROSS-REFERENCE TO RELATED APPLICATION

The present application is a continuation-in-part of U.S. patent application Ser. No. 11/165,593, filed Jun. 22, 2005, which has issued as U.S. Pat. No. 7,618,413, the benefit of which is hereby claimed under 35 U.S.C. §120 and is fully incorporated by reference.

BACKGROUND

The present invention relates to medical devices in general and, in particular, to devices for manipulating steerable medical devices or other minimally invasive tools within a patient's body.

Steerable medical devices and other minimally invasive surgical tools are being increasingly used to perform medical procedures inside a patient's body. Steerable devices generally include an elongated shaft and one or more control cables having distal ends secured at or adjacent the distal tip of the shaft. A control knob or lever selectively tightens the control cables in order to bend the device in a desired direction. The problem with most medical device controllers is that they require two hands in order to move the distal tip of a device in more than one plane. Alternatively, in those designs where a user can move the distal tip in four directions with one hand, two hands are still required in order to advance, retract, or rotate the device. Although some robotic systems have been proposed to allow a physician to direct a distal tip of a device in any direction using motors, these systems are generally expensive and complicated.

SUMMARY

The present invention is a control system for selectively orienting the distal tip of a steerable medical device. In one embodiment, the control has a body with an actuator that can be independently moved in at least two directions so movement of the actuator in each direction moves the distal tip of the medical device in a plane. In one embodiment, the control may be mounted on a rail that is fixed with respect to the location of a patient such that advancement or retraction or rotation of the actuator body on the rail causes a corresponding advancement, retraction, or rotation of the medical device. In one particular embodiment, the actuator allows movement of the distal tip in one plane to be decoupled from movement in another plane.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
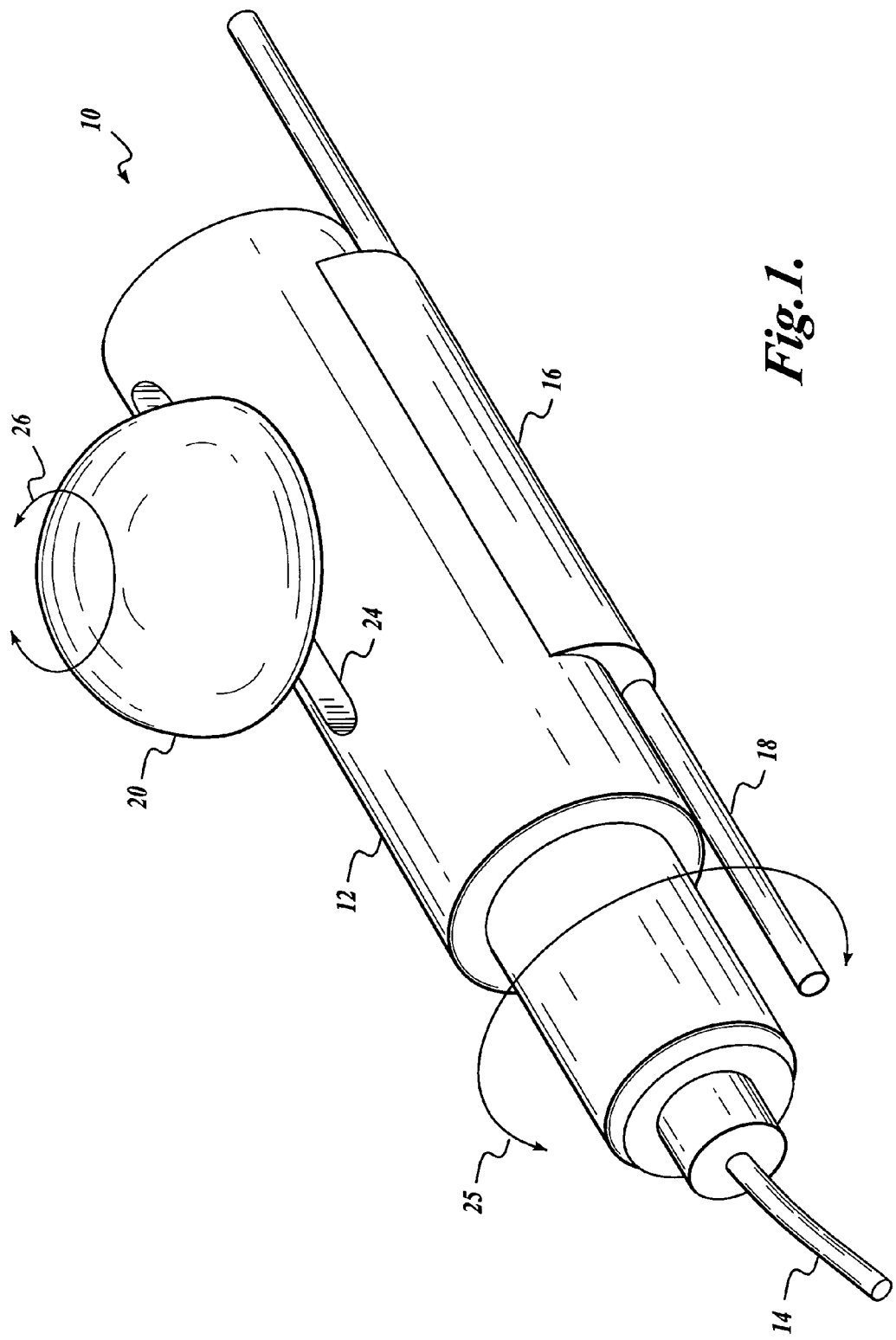
FIG. 1 is an elevated isometric view of a medical device control system in accordance with one embodiment of the present invention.

As indicated above, the present invention is a control system for selectively orienting a steerable medical device in a number of directions. In one embodiment of the invention, the control 10 includes a ergonomic, generally cylindrical body 12 having an actuator (described below) that operates to selectively tighten or release control cables that cause the distal tip of a medical device 14 such as a catheter, visualization device or instrument to bend in a desired direction. The control body 12 includes one or more clamps 16 that allow it to be moved along a length of a rail 18 in order to advance or retract the medical device 14 as well as to provide rotation of the medical device around its longitudinal axis. The clamps 16 may provide a friction force that is overcome by a user in order to move the control body 12 along the rail 18. Alternatively, the clamps 16 may include release mechanisms such as a brake or lock that should be loosened to adjust the position of the control body 12 with respect to the rail 18. In yet another embodiment, the clamps 16 and rail 18 may include a gear to move the control body 12. The rail 18 may be clamped to a patient table or otherwise remain fixed with respect to the location of the patient such that the position of the medical device 14 remains constant if the physician's hand is removed from the control 10.

The control 10 can be rotated about the longitudinal axis of the rail 18 in the direction of the arrow 25 in order to impart rotational motion or torque to the medical device 14. Although the center axis of the medical device 14 is offset from the central axis of the rail 18, the medical device 14 is usually routed through a guiding device such as an endoscope or other constraining mechanism such that movement of the control 10 about the axis of the rail 18 causes the distal tip of the medical device 14 to rotate around the longitudinal axis of the device.

The control 10 also includes an actuator 20 that is used by a physician, or their assistant, in order to move the distal tip of the medical device 14 in one or more of the up/down or right/left directions. In one embodiment, the actuator 20 can be moved forward or backward within a slot 24 that extends longitudinally along the top of the body 12 in order to move the distal tip of the medical device 14 up or down. In addition, the actuator 20 can be rotated as indicated by the arrow 26 in order to move the distal tip of the medical device in the right/left directions. As will be explained in further detail below, movement of the distal tip in the up/down direction is decoupled from movement of the distal tip in the right/left direction so that a physician can maintain the orientation of the distal tip in the up/down direction while changing the right/left orientation or vice versa. Using the control 10, the physician is able to adjust the orientation of the distal tip of the medical device with one hand.

Figure 2:
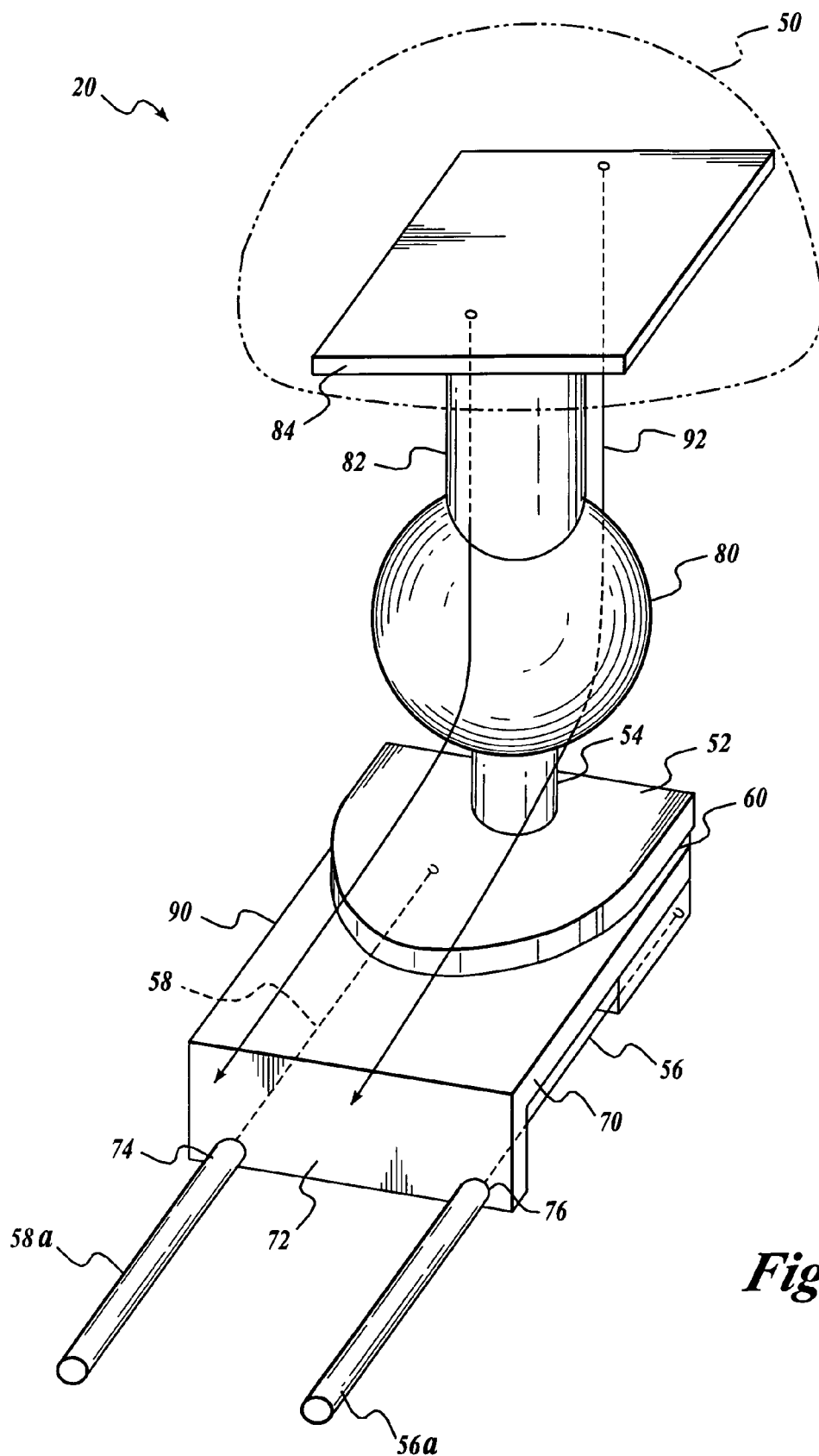
FIG. 2 illustrates one embodiment of an actuator for moving a medical device in accordance with the present invention.

As indicated above, this embodiment of the control 10 allows an operator to adjust the orientation of a medical device with four degrees of freedom (up/down, left/right, forward/backward and rotationally) using one hand. FIG. 2 illustrates one embodiment of an actuator 20 for allowing a physician to change the up/down and right/left orientation of a distal tip of a medical device. The actuator 20 has a cap 50 that is connected to a cable guide plate 52 through a shaft 54. Rotation of the cap 50 about the longitudinal axis of the shaft 54 causes tension of one pair of control cables 56, 58. Tension of the control cable 56 causes a medical device tip to bend in the left direction, while tension on a control cable 58 causes a medical device tip to move in the rightward direction. The cable guide plate 52 is generally semi-circular in shape, with a rounded front end and a groove 60 therein to guide the corresponding control cables 56, 58. In the embodiment shown, the rear face of the cable guide plate 52 is generally flat. The ends of the control cables 56, 58 may be either fixedly secured to the cable guide plate 52 or slidably secured to the guide plate. If fixedly secured to the cable guide plate 52, then one control cable is tensioned while the other control cable is compressed as the cable guide plate 52 is rotated by the cap 50. If the ends of the control cables are slidably secured to the cable guide plate 52, then one control cable is tensioned and the other is released from tension as the cable guide plate 52 is rotated. In some embodiments, the cables 56, 58 may be a single cable wound around the guide plate 52. In some embodiments, the medical device 14 is permanently secured to the body 12 of the control 10. In other embodiments, the medical device is releasably secured to the body 12 by including cable connectors or the like that join the control cables in the medical device to the control cables in the body 12.

Also secured to the shaft 54 at a location adjacent the control cable guide plate 52 is a stop plate 70. The stop plate 70 has a raised lip 72 with a pair of holes 74, 76 therein through which the control cables 56, 58 are passed. Each of the control cables 56, 58 are preferably bowden cables, whereby the holes 74, 76 are sized such that the inner control cable of the bowden-type cables passes through the holes but the outer sheaths 56a, 56b of the bowden cables are too large to fit through the holes 74, 76. In one embodiment, the stop plate 70 is shaped so that it does not rotate in the body of the control 10 when the actuator 20 is rotated around the axis of the shaft 54, but does move within the body of the control as the actuator 20 is tilted back and forth. The stop plate 70 allows the physician to adjust the left/right position of the medical device 14 without adjusting the up/down position or vice-versa as will be explained below.

A ball joint 80 on the shaft 54 cooperates with a corresponding socket (not shown) in the interior of the body 12 of the control 10. A collar 82 extends between the ball joint 80 and the cap 50 whereby the shaft 54 can rotate within the collar 82. A top plate 84 is secured to the other end of the collar 82 and has a hole through which the shaft 54 is passed. The top plate secures the proximal ends of a pair of control cables 90, 92 that control the up/down movement of the medical device. The ball joint 80 allows the actuator 20 to be tilted back and forth with the interior of the body 12. Movement of the cap 50 towards the proximal end of the control 10 causes the control cable 90 to tighten, thereby causing the distal end of the medical device to move upwards. Pushing the cap 50 in the direction of the distal end of the control 10 causes the control cable 92 to tighten thereby causing the distal end of the medical device to move downwards.

Movement of the actuator 20 forwards and backwards about the axis of the ball joint 80 does not cause the distal tip of the medical device to move in the left/right direction. Similarly, rotation of the cap 50 about the longitudinal axis of the shaft 54 does not cause movement of the distal tip in the up/down direction. Therefore, the orientation of the medical device can be independently controlled in the up/down or right/left directions.

In some instances the control cables may be difficult to move with manual power alone. Therefore the actuator 20 may include a power assist mechanism to aid in tensioning the control cables. Such power assist may include hydraulic or pneumatic actuators, electric motors, magnets etc. that provide the additional force required to orient the distal tip of the medical device 14 in the desired direction.

Figure 3A:
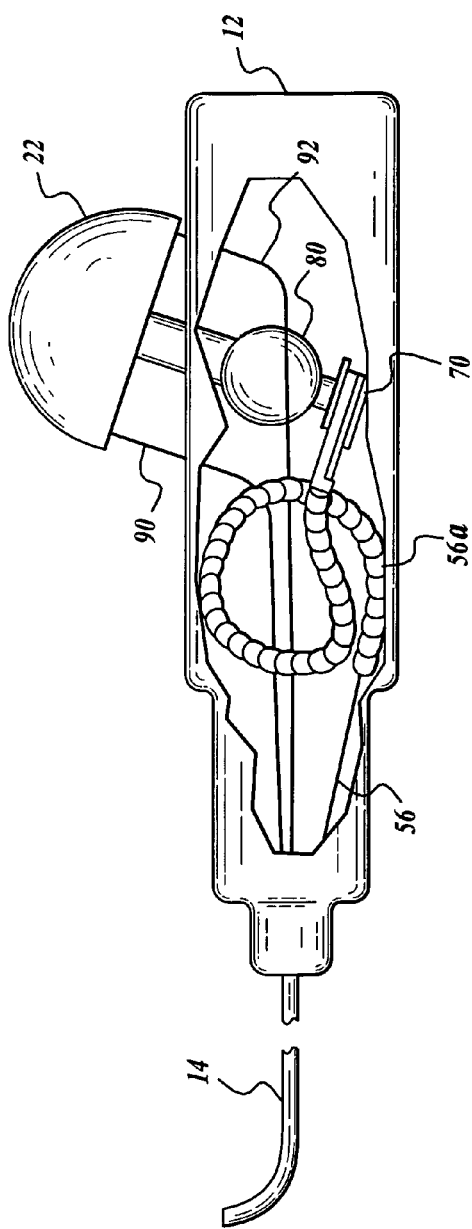
FIGS. 3A and 3B illustrate how an embodiment of the invention isolates movement of the distal tip of a controlled medical device.
Figure 3B:
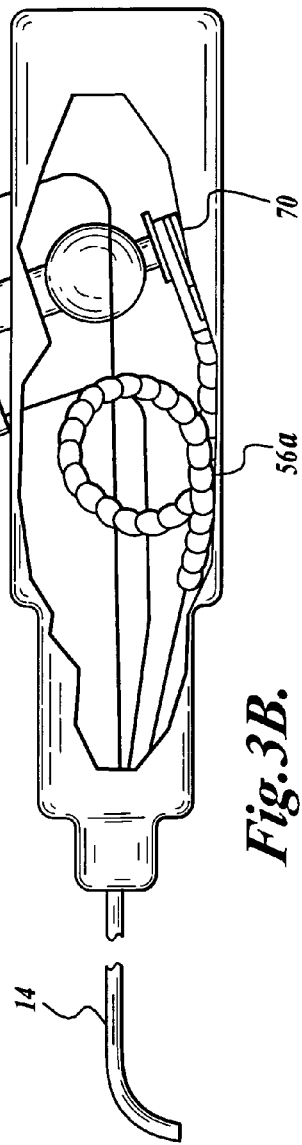

FIGS. 3A and 3B illustrate how movement of the distal tip of the medical device 14 in the left/right direction is decoupled from movement of the medical device in the up/down direction. In the embodiment shown, the control cables 56, 58 controlling the left/right movement of the medical device 14 pass through the stop plate 70. Positioned over the control cables are the outer sheaths 56a, 58a of the bowden cables (see FIG. 2). The distal ends of the outer sheaths 56a, 58a are fixed with respect to the distal end of the medical device 14. The proximal ends of the outer sheaths 56a, 58a are joined to the stop plate 70 and move with the cable guide plate 52, as it is moved back and forth within the body 12. For example, control cable 56 has an outer sheath 56a having one end secured to the stop plate 70 and another end abutting the internal wall of the body 12, as shown in FIG. 3A. The outer sheath 56a is looped to have enough slack such that as the actuator 20 is tilted or moved, the slack in the outer sheath 56a is adjusted. As will be appreciated by those skilled in the art, the amount of bend imparted by the control cables 56, 58 to the distal tip of a medical device 14 depends upon the position of the ends of the control cables 56, 58 with respect to a proximal end of the outer sheaths 56a, 58a of the bowden cables. Because the outer sheaths include a loop or slack that allows them to move as the actuator 20 is moved, this distance does not change as the actuator 20 is tilted forward and back in the body 12. Therefore, a user can adjust the up/down direction of the medical device 14 by tilting the actuator 20 forwards and backwards, as indicated in FIG. 3A and FIG. 3B, while not changing the orientation of the distal tip medical device in the left/right direction. In some cases, it may be desirable to limit the movement of the looped bowden cables to prevent them from becoming pinched. Therefore, the body 12 of the controller may include a slot or other restraint to limit the movement of the outer sheaths of the control cables.

Although the presently disclosed embodiment of the control operates the left/right direction by rotating the cap 50 around the axis of the shaft 54, it will be appreciated that the control cables could be arranged such that rotation of the cap causes the tip to move in the up/down direction and movement of the actuator 20 back and forth causes movement in the left/right direction. Alternatively, the actuator 20 could include nested, rotatable knobs to control both the up/down and left/right directions in a manner similar to that found in conventional endoscopes. If desired, the position of the medical device in the left/right direction can be fixed with brakes, mechanical stops, or a sufficient friction force on the cap 50 so that once the desired left/right position of the medical device is determined, the position of the medical device can remain fixed if the user releases the actuator. Alternatively, a braking force can be applied to the medical device control cables in order to fix the position of the medical device. Similarly, the position of the medical device in the up/down direction can be fixed by inhibiting movement of the actuator in the forward and aft directions, or by applying a braking force to the control cables.

Figure 4:
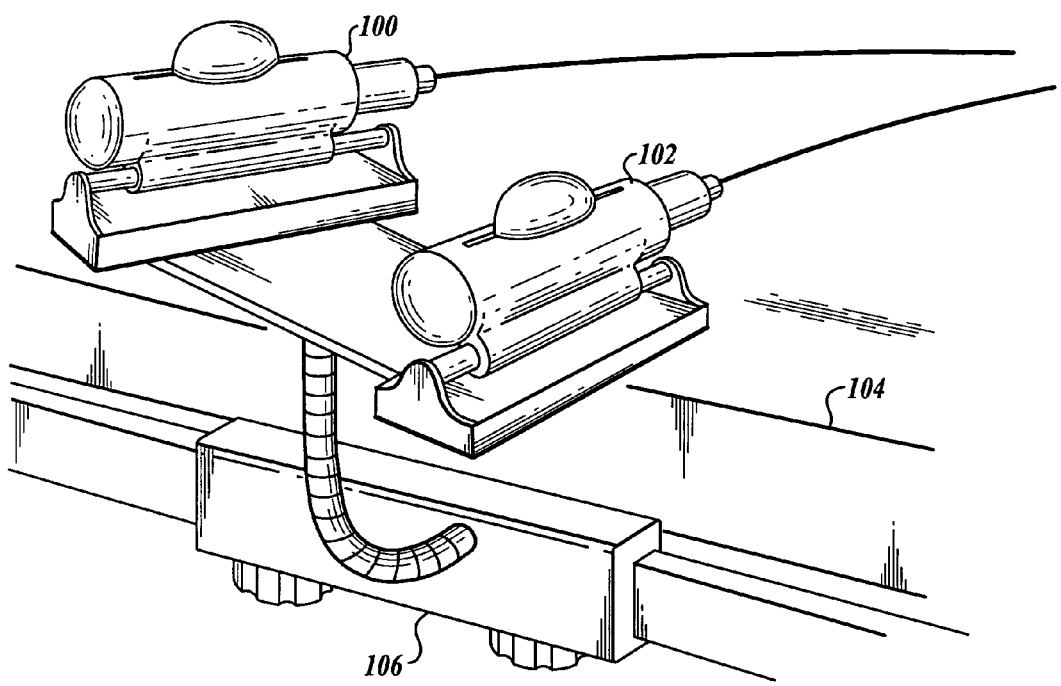
FIG. 4 illustrates how two control systems can be used by a physician.

FIG. 4 illustrates how a pair of controls 100, 102 can be secured at a fixed position with respect to a patient such as on a patient table 104 in order to allow a physician to control the orientation of a pair of medical devices. The medical devices preferably include one or more integrated instruments such as biopsy forceps, cauterizers, snares, scalpels, scissors, graspers, needle holders, staplers, fiber optic or solid state imagers etc. contained therein. Alternatively, the medical devices may be catheters that include or more lumens through which instruments can be routed. A moveable gooseneck 106 allows the position of the controls 100, 102 to be changed. Although the rails of the controls 100, 102 are shown connected to the gooseneck 106 with a pair of bases, it will be appreciated that the rails may be connected directly to a gooseneck or table 104, if desired. In yet another embodiment, one or more of the controls 100, 102 may be secured to the patient such as by strapping the controls to the patient's leg, torso, head etc. In other embodiments, the controls may be secured to the operator's body or to an endoscope or guide tube that is used in the patient.

Figure 5:
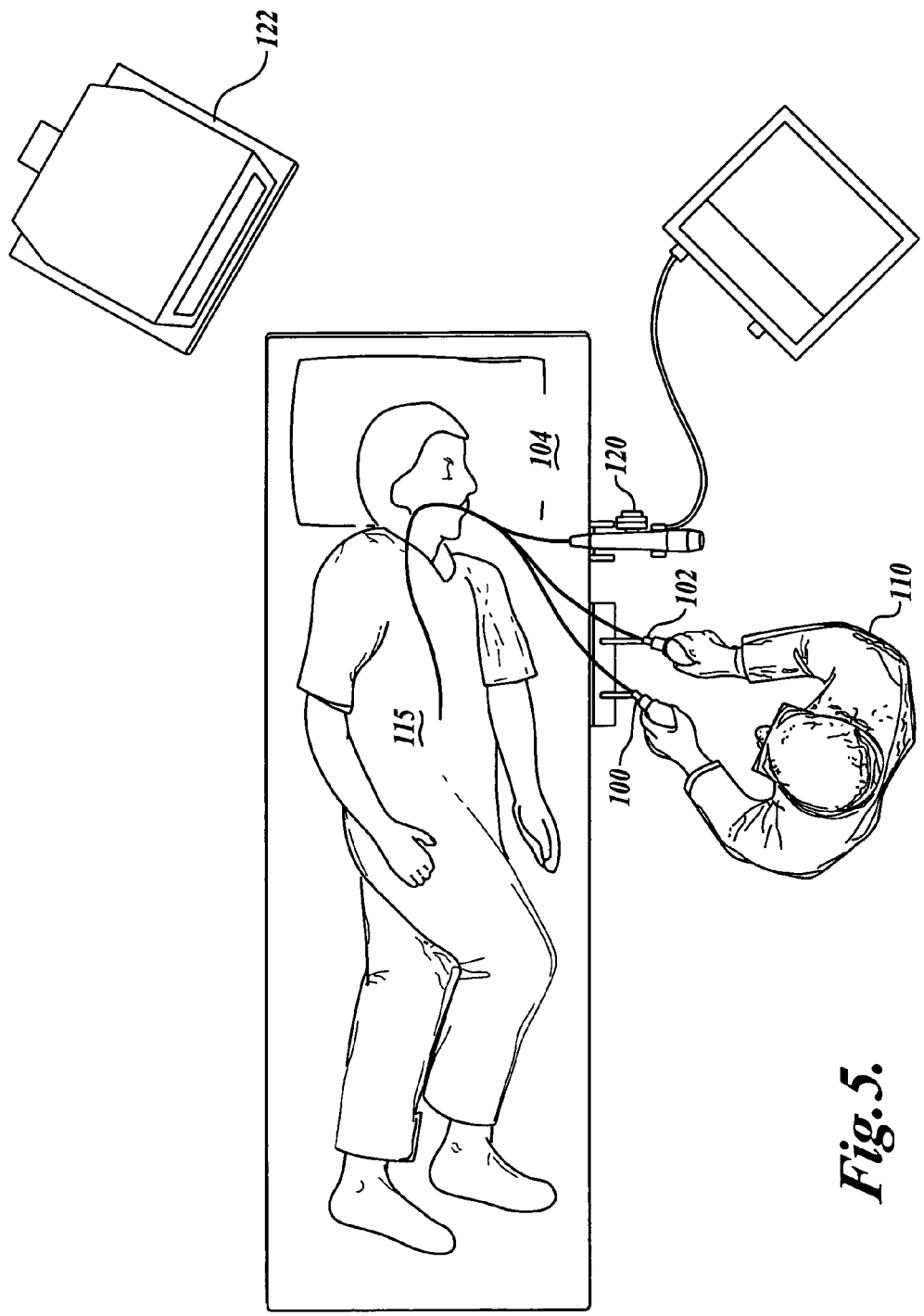
FIG. 5 illustrates how a physician operates a control system with each hand.

FIG. 5 illustrates how a physician 110 can use two hands to manipulate the pair of controls 100, 102 in order to perform a procedure within a patient 115. In practice, the medical devices controlled by the controls 100, 102 are often used in conjunction with a visualization device such as an endoscope 120 that produces images on a monitor 122 so that the physician can view the procedure. The present invention allows a physician to use two hands to control two medical devices in order to perform examinations or surgical procedures in the GI tract, colon, lungs, or through another orifice of the patient. Alternatively, the medical devices can be inserted through an incision such as with a trocar to access other areas of the body.

FIGS. 6A-6E illustrate another embodiment of a control system for selectively orienting a medical device in accordance with the present invention. In this embodiment, a control 140 is slidably connected to a rail 142 with a pair of clamps 148 and 150. The clamps allow the actuator 140 to move lengthwise along the rail 142. In one embodiment, the clamps 148 and 150 allow the control 140 to be rotated about the longitudinal axis of the rail 142. The control 140 includes an actuator handle 160 that allows a user to control the orientation of a distal tip of a medical device 250 as will be explained below. The handle further includes a trigger 164 that allows a user to actuate a tool within the medical device 250.

Figure 6A:
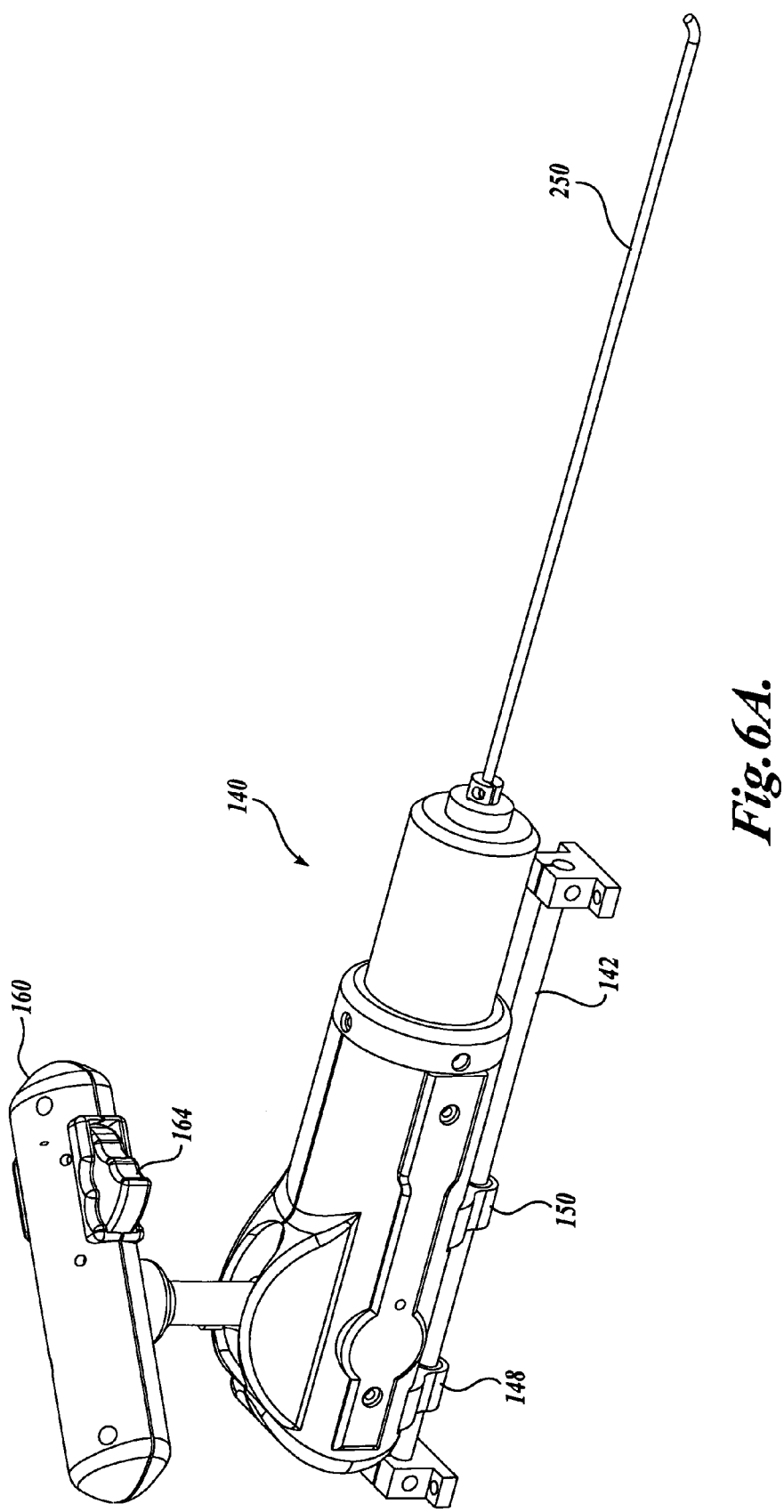
FIGS. 6A-6F illustrate another embodiment of a control system for moving a medical device in accordance with the present invention.
Figure 6B:
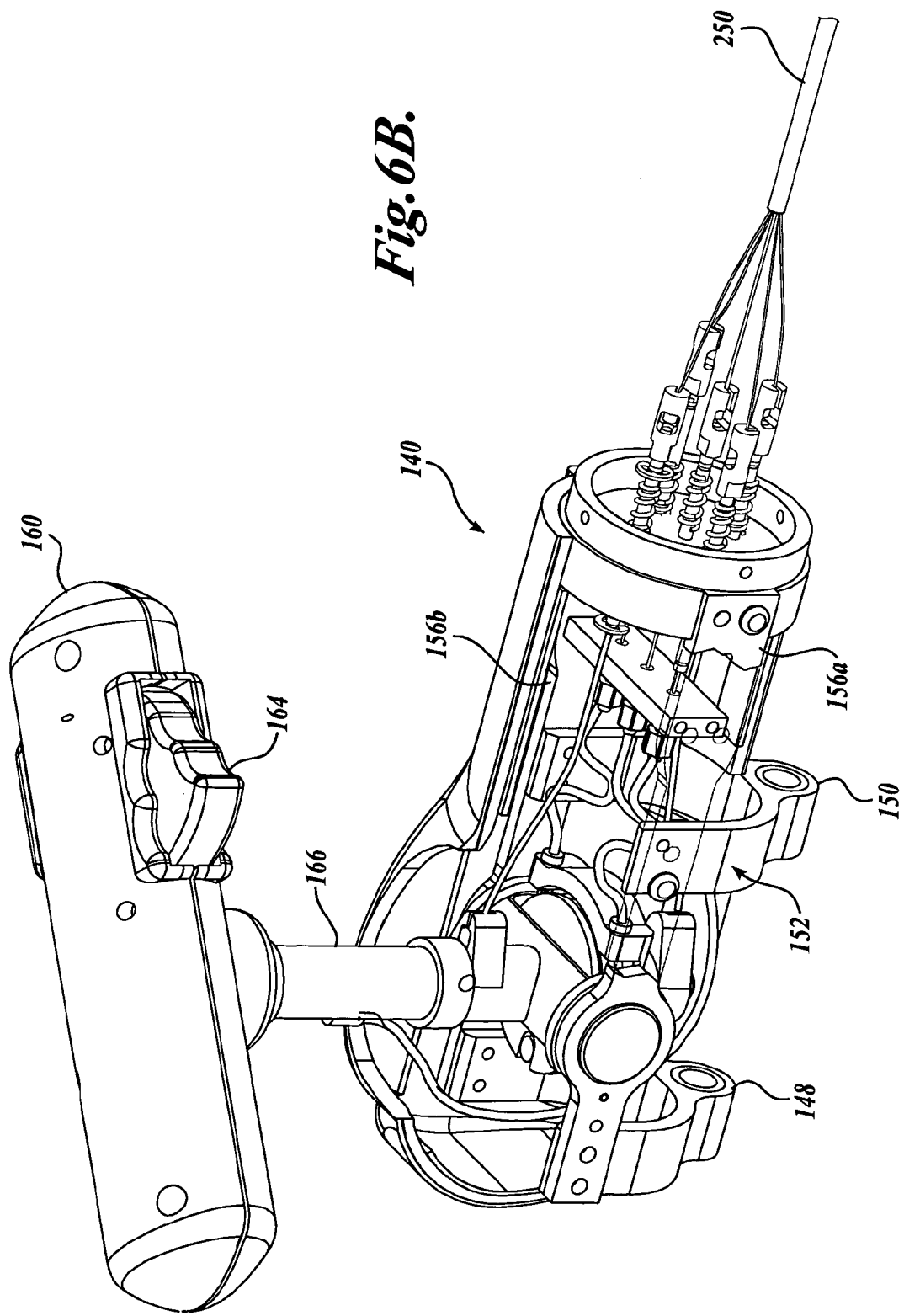

FIG. 6B illustrates further details of a control 140 in accordance with an embodiment of the present invention. The control 140 is coupled to the rail with one or more U-shaped clamps 148 and 150. Each of the U-shaped clamps includes a pair of spaced-apart arms 152 that are connected to a pair of side rails 156a, 156b that extend for the length of the control and form a frame to which additional components of the control can be secured. The arms of the clamps 148, 150 are secured to the side rails 156a, 156b with a fastener such as a rivet, screw, adhesive, or the like. The actuator handle 160 is rotatably coupled to the side rails 156a, 156b such that the handle is able to move forward and aft within the control 140. In addition, the handle 160 can rotate about a longitudinal axis of a shaft 166. Movement of the handle back and forth causes the distal tip of the medical device 250 to move in one plane while rotation of the actuator handle 160 about the longitudinal axis of the shaft 166 causes movement of the distal tip of the medical device 250 in another plane.

Figure 6C:
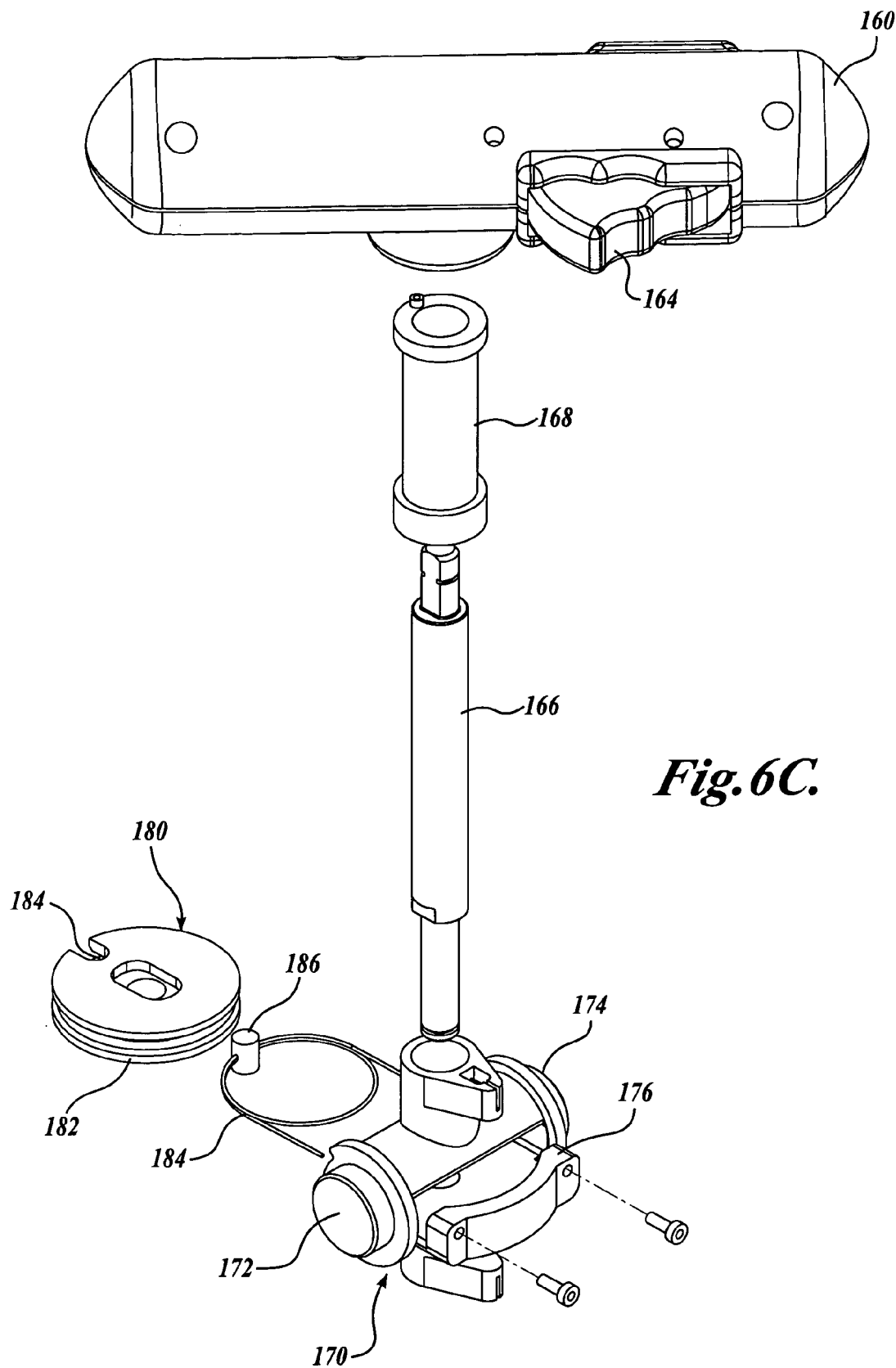

FIG. 6C illustrates further detail of the actuator handle 160. As indicated above, the handle is secured to the pair of side rails 156a, 156b with a trunnion 170 shown in FIG. 6B. A trunnion 170 includes a pair of outwardly extending posts 172, 174 that fit in corresponding holes formed in the side rails 156a, 156b. A locking mechanism such as a snap ring or other fastener secures the posts 172, 174 into the side rails. The handle 160 is rotatably secured to the trunnion 170 with a shaft 166. A collar 168 fits over the shaft between the trunnion 170 and the handle 160. The collar 168 provides a stop for a bowden-type cable as will be described in further detail below. The trunnion 170 further includes a stop plate 176 that provides an anchor for the ends of the bowden-type cables in the same manner as the stop plate 70 shown in FIG. 2. The stop plate 176 pivots back and forth with the posts 172, 174 as the handle 160 is moved back and forth in the control. The trunnion 170 further includes a slot in the center of the trunnion and between the posts 172, 174 in which a cable guide plate or disk 180 is located. In this embodiment, the cable guide plate 180 is generally circular and includes a groove 182 therein in which an actuating cable 184 is fitted. The cable guide plate 180 includes a notch 184 that receives a corresponding cable stop 186 that is secured to the cable 184. The cable is wrapped around the cable guide plate 180 and includes a pair of legs that are coupled directly and indirectly to the distal end of the medical device. Movement of the cable guide plate causes corresponding tension or relaxing of the legs of the cable 184. The cable guide 180 is fitted into a slot within the trunnion such that it lies behind the stop plate 176. The shaft 166 fits through a corresponding hole in the cable guide plate 180 and a snap ring or other fastening mechanism secures the components together. Rotation of the handle 160 causes a corresponding rotation of the shaft 166 which in turn is coupled to the cable guide plate 180 to tension or release the legs of the actuating cable 184.

Figure 6D:
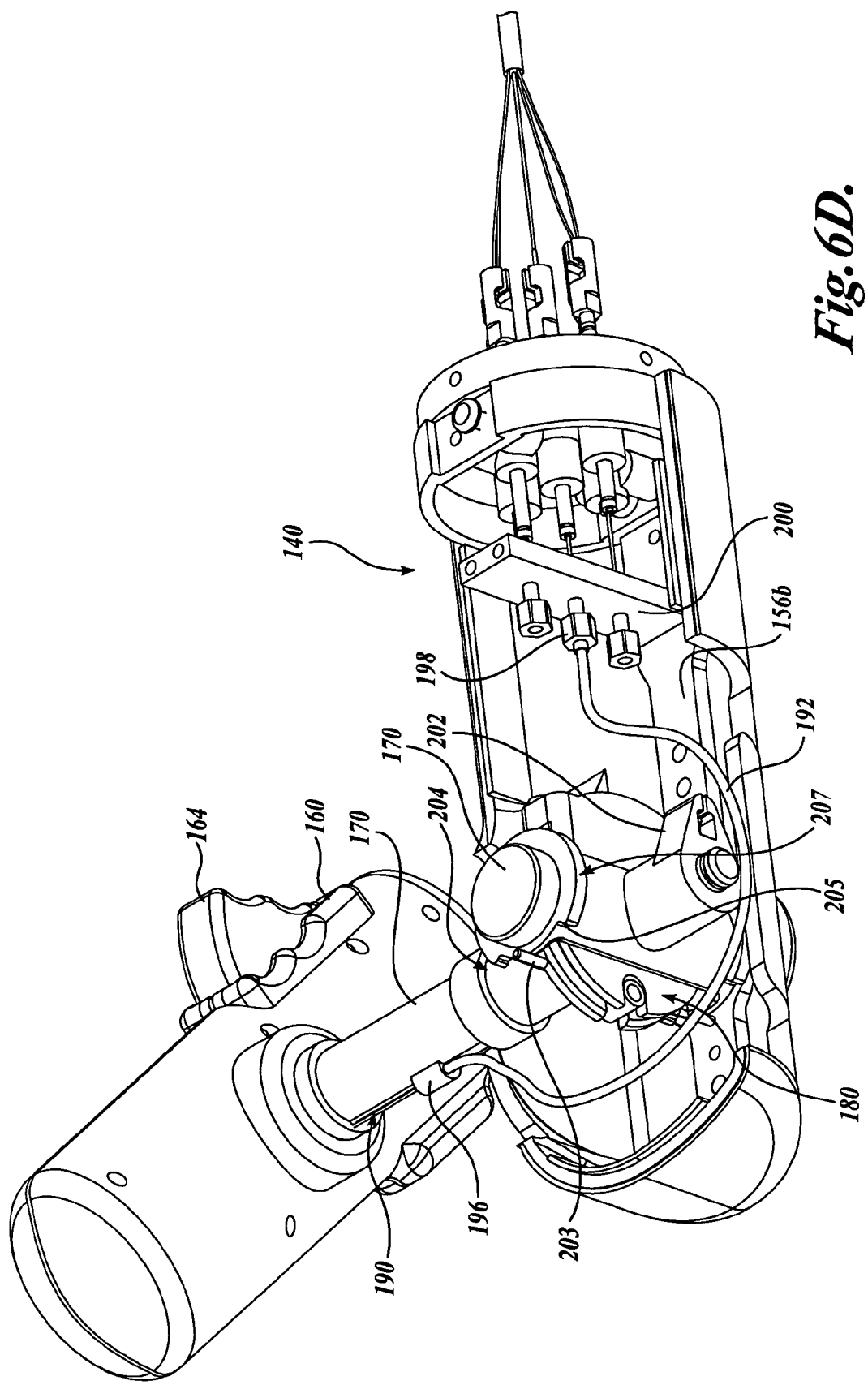

FIG. 6D illustrates further detail of the trunnion 170 within the control 140. The cable guide plate 180 is fitted within the slot of the trunnion 170 and rotates back and forth within the slot by rotation of the actuator handle 160. To limit the amount of forward and aft movement of the handle 160 in the control, a ring 207 that fits over the posts of the trunnion 170 has a notch 205 therein. A pin 203 secured in the side rail (not shown) limits how far the handle can travel by engaging the ends of the notch 205.

Also shown in FIG. 6D is a cable 190 that is actuated by the trigger mechanism 164 on the handle. Depressing the trigger 164 causes a tensioning of the cable 190 to actuate a tool within the medical device. In the embodiment of the invention illustrated, the cable 190 is a bowden-type cable having an outer sheath 192 with one end secured to a cable stop 196 positioned on the collar 168 that is fitted over the shaft 166. The other end of the bowden cable joins a stop 198 that is fitted within a crossbar 200 extending between the pair of side rails 156a, 156b.

The crossbar 200 also includes stops for the bowden-type cables that are driven by rotation of the handle as described above.

As shown in FIG. 6D, the trunnion also includes a shaft that extends in a direction perpendicular to the posts that are coupled to the side rails. The shaft includes a pair of cable receivers 202, 204 having a slot or other receptacle therein that secures an end of an actuation cable. One of the cable receivers 204 is below the pivot point of the trunnion 170, and the other is above the pivot point. Upon tilting the trunnion 170 in the control 140, the cable receivers 202, 204 selectively tension or release control cables that move the distal tip of the medical instrument 250 in a plane.

Figure 6E:
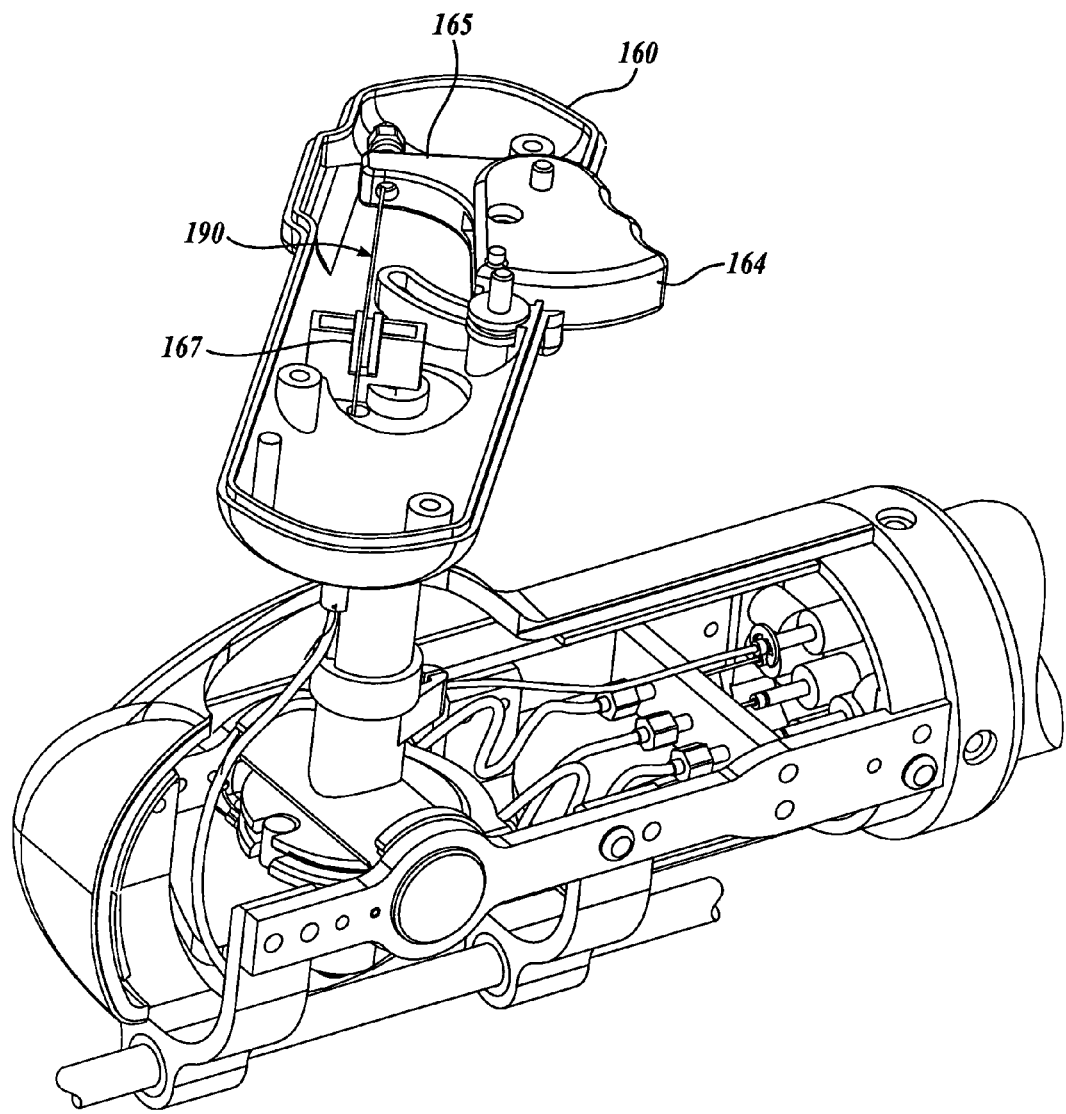

Further detail of one embodiment of a trigger mechanism 164 is shown in FIG. 6E. In this embodiment, the trigger 164 is rotatably received within the handle 160 such that squeezing the trigger 165 causes it to rotate about a pivot point. The trigger 160 includes an outwardly extending arm 165 to which an end of the actuation cable 190 is secured. As the arm is moved by pressing the trigger, tension on the control cable 190 is increased to actuate the tool at the end of the medical device. A roller or pulley 167 changes the direction of the control cable 190 from within the handle to a direction that extends along the shaft 166.

Figure 6F:
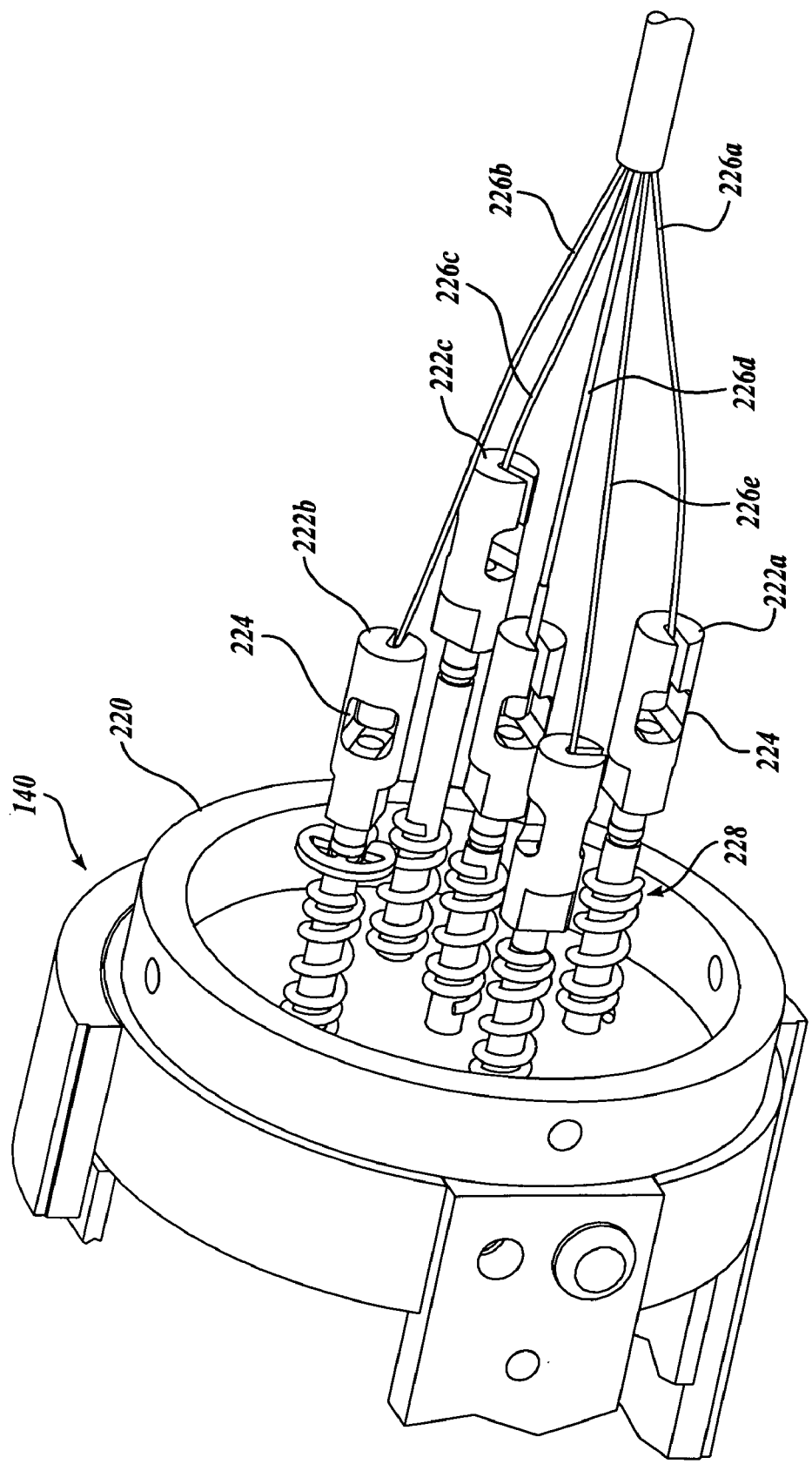

FIG. 6F illustrates one embodiment of a coupling mechanism that can be used to selectively couple the control 140 to one or more control wires within the medical device 250. The coupler 220 forms an end-wall that is positioned within the actuator housing 140 between the support rails 156a, 156b. The coupler 220 has a number of spring loaded pins 222a, 222b, 222c, etc., positioned therethrough. Each of the pins 222a, 222b, 222c, etc., is connected to a control cable that is moved by the handle 160 or the trigger mechanism 164 as described above. Each pin includes a cable receiving notch 224 therein that receives the ball or stop at the end of a corresponding control cable 226a, 226b, 226c, etc. for the medical device. Secured by a cable ball in the slots 224, each pin allows the tensioning or release of the corresponding cables 226a, 226b, 226c, etc. In the embodiment shown, each of the pins 222a, 222b, 222c, etc. includes a spring 228a, 228b, 228c that biases the pin toward the distal end of the control 140. The springs 228 serve to tension the control cables within the body of the control when not being pulled by the actuator.

To connect a medical device 250 to the control 140, the ball ends of each of the control cables 226a, 226b, 226c, etc. are inserted into each of the cable receiving slots 224 of the corresponding pins. Similarly, to disconnect the cable, the balls or cable ends are removed from the cable receiving slots 224. Upon completion of a procedure, the medical device 250 can be uncoupled from the control 140, cleaned or sterilized for re-use or thrown away.

FIGS. 7A-7I illustrate a number of alternative trigger mechanisms that allow a tool to be actuated from the control that orients a medical device in the up/down, right/left, forward/backward, and rotational directions.

Figure 7A:
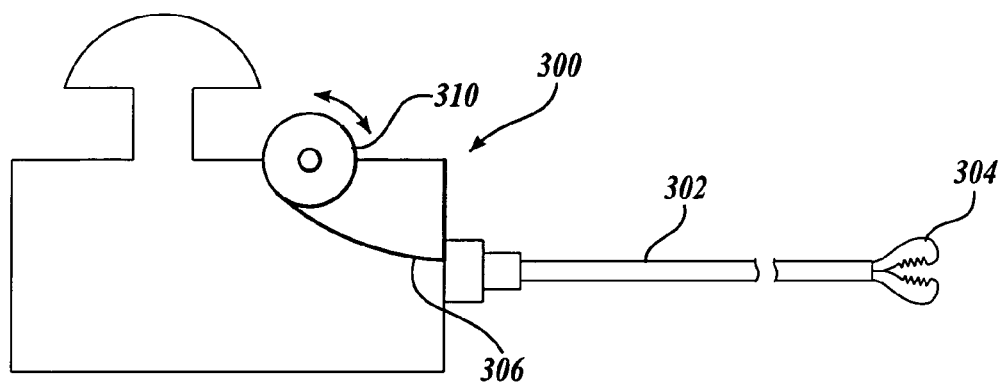
FIGS. 7A-7I illustrate a number of alternative trigger mechanisms for actuating a tool in accordance with embodiments of the present invention.

FIG. 7A illustrates one embodiment of a trigger mechanism for use with an actuator 300. In this embodiment, the actuator 300 controls the orientation of a shaft 302 of a steerable medical device in the manner described above. The shaft 302 includes a tool such as biopsy forceps 304 that is operated by selectively tensioning or releasing a control wire 306. In this embodiment, the trigger mechanism includes a thumb wheel 310 about which the control wire 306 is wound. Movement of the thumb wheel 310 about an axle winds or unwinds the control wire 306 on the thumb wheel, thereby tensioning or releasing the control wire coupled to the jaws of the biopsy forceps 304.

Figure 7B:
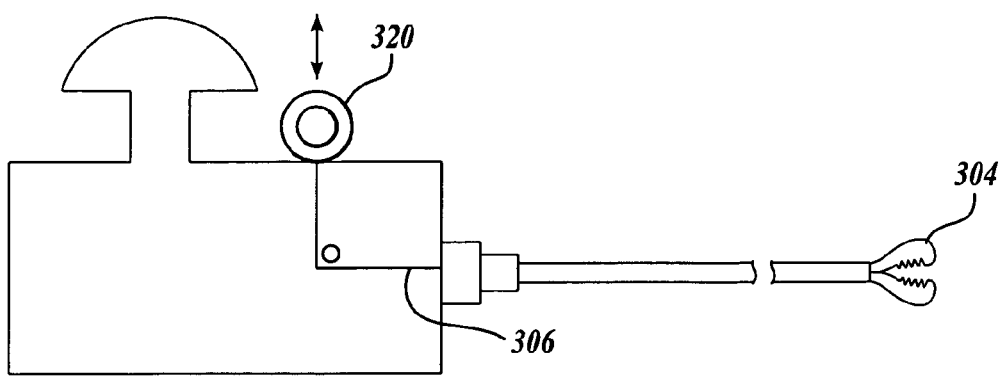

FIG. 7B illustrates another embodiment of a trigger mechanism for activating a tool such as a biopsy forceps 304 at the distal end of a steerable medical device. In this embodiment, a control wire 306 is connected to a pull ring 320 at one end and to the tool at the other end. Selective tensioning and releasing of the pull ring 320 tightens or releases the control wire 306. In some embodiments, the control wire 306 or the pull ring 320 may be spring biased to return the control wire to either the tensioned or untensioned state.

Figure 7C:
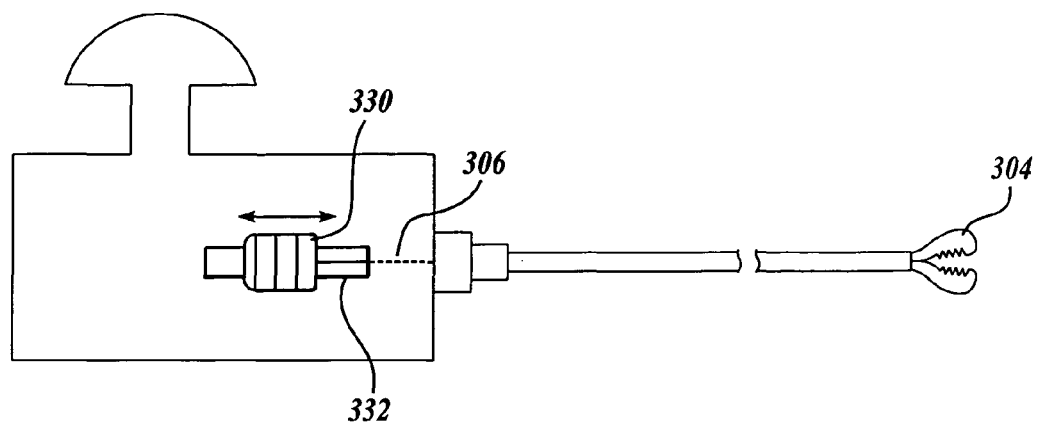

FIG. 7C illustrates another embodiment of a trigger mechanism for operating a tool such as a biopsy forceps 304 at the distal end of a steerable medical device. In this embodiment, a slider 330 is coupled to the control wire 306 that operates the biopsy forceps 304. The slider 330 is movable within a slot 332 on the control. Movement of the slider 330 in the proximal direction tensions the control wire 306. Similarly, movement of the slider 330 in a distal direction selectively releases the control wire 306 to activate the tool.

Figure 7D:
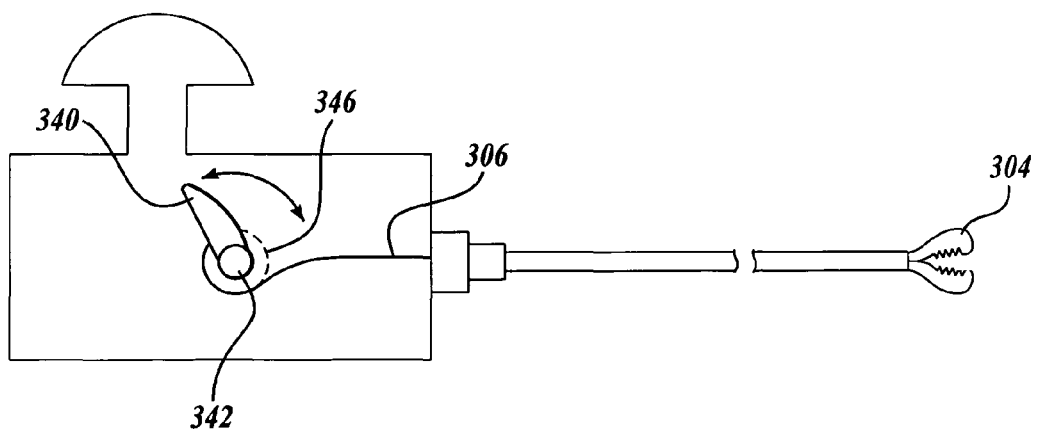

FIG. 7D illustrates yet another embodiment of a trigger mechanism for operating a tool such as a biopsy forceps 304 at the distal end of a steerable medical device. In this embodiment, a control wire 306 that operates the biopsy forceps 304 is connected to a switch type mechanism 340. Movement of the switch about a pivot point 342 causes the control wire 306 to be wound or unwound around a spool 346 that is coupled to the switch 340. With the control wire 306 wound around the spool 346, tension on the control wire is increased, while unwinding the control wire 306 from the spool 346 causes the tension to be released in order to operate the biopsy forceps 304.

Figure 7E:
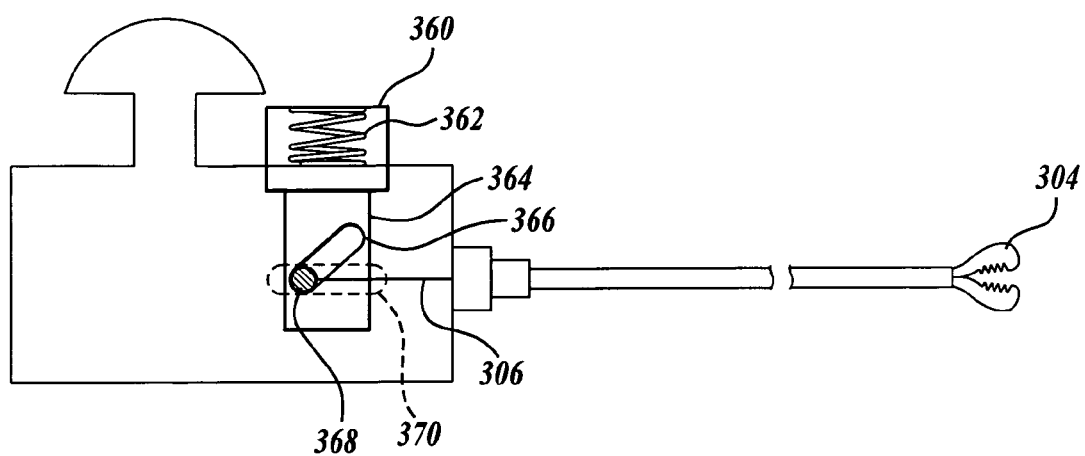

FIG. 7E illustrates yet another alternative embodiment of a trigger mechanism for controlling a biopsy forceps 304 at the distal end of a steerable medical device. In this embodiment, a trigger mechanism includes a push button 360. The push button 360 is preferably biased with a spring 362 that causes the button to return to a predefined state. Coupled to the push button 360 is a shaft 364 including an angled slot 366 therein. A post 368 connected to the drive cable 306 moves within a slot 370 that is longitudinally aligned with the actuator and in the angled slot 366. The angled slot 366 on the shaft 364 moves the post 368 back and forth within the slot 370 as the push button 360 is moved up and down in order to actuate the biopsy forceps 304.

Figure 7F:
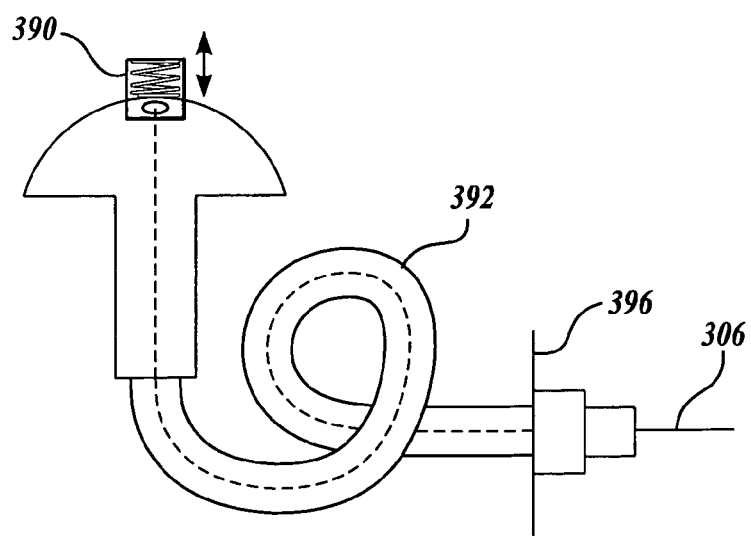

In some embodiments, the push button may be located on the handle of the actuator. As shown in FIG. 7F, a button 390 actuates a cable 306, where the cable includes an outer bowden cable sheath 392 positioned between the actuator and a fixed position 396, for example, within the actuator (not shown). Pushing the button 390 tightens or releases the cable 306 that controls the tool that is actuated with the cable 306.

Figure 7G:
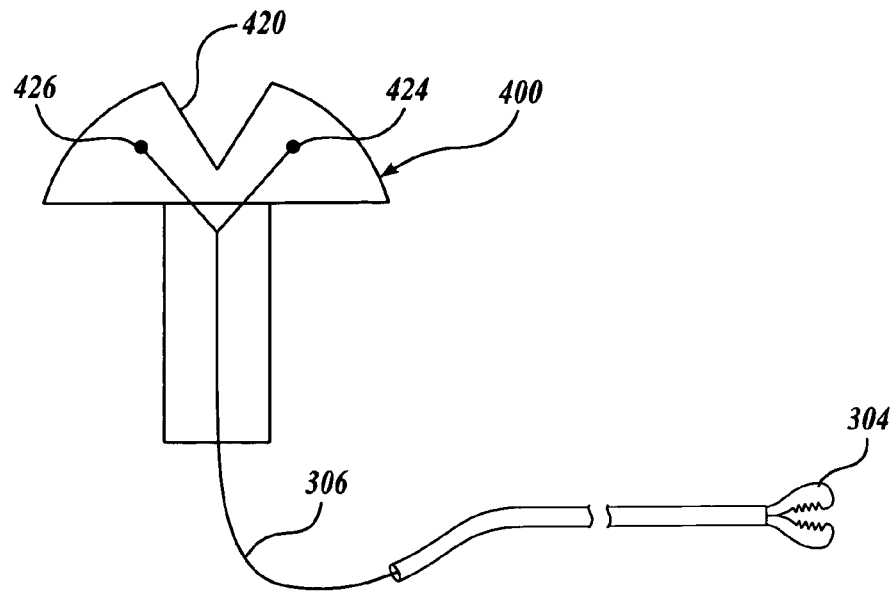

FIG. 7G shows yet another embodiment of a trigger mechanism for actuating a tool such as a biopsy forceps from a control. In this embodiment, the handle 400 of the control includes a V-shaped groove 420 that separates portions of the handle. The handle 400 is flexible so that the V-shaped groove can be collapsed or expanded. A control cable 306 is split in a Y-type configuration wherein each leg of the Y is contained in a different side of the V-shaped groove in the handle. Compression of the handle 400 about the V-shaped groove 420 causes the end points of the cable 424, 426 to move toward one another, thereby lengthening the cable. Upon expansion of the V-shaped groove, the end points 424, 426 of the control cable 306 are spread apart, thereby shortening the cable and actuating a tool. The handle 400 may be made of a plastic material that allows it to bend. Alternatively, the handle may include a hinge mechanism to allow it to bend.

Figure 7H:
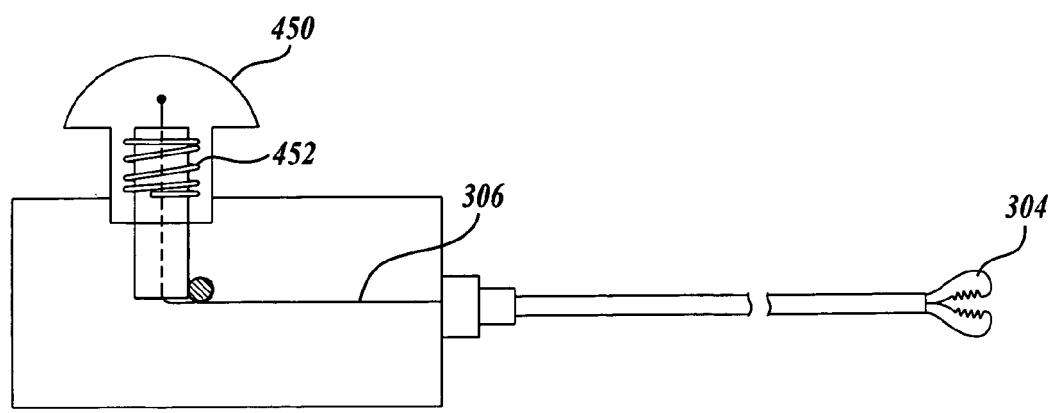

FIG. 7H shows yet another alternative embodiment of the trigger mechanism for actuating a cable 306 connected to a biopsy forceps 304 or other tool at the distal end of a steerable medical device. In this embodiment, a handle 450 is spring loaded so that it can be pressed downwards. A control cable 306 has an end coupled to the handle such that pressing the handle releases tension on the control cable. Releasing the handle increases tension on the control cable 306 to actuate the biopsy forceps.

Figure 7I:
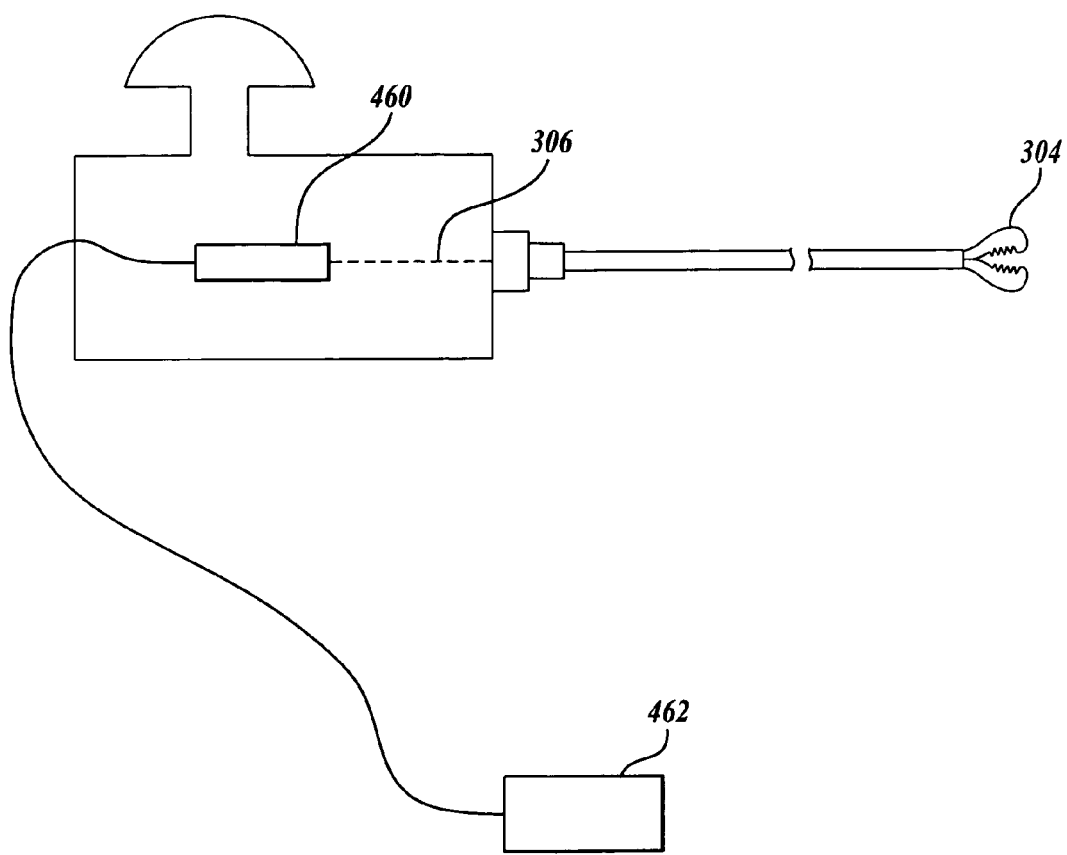
Figure 8:
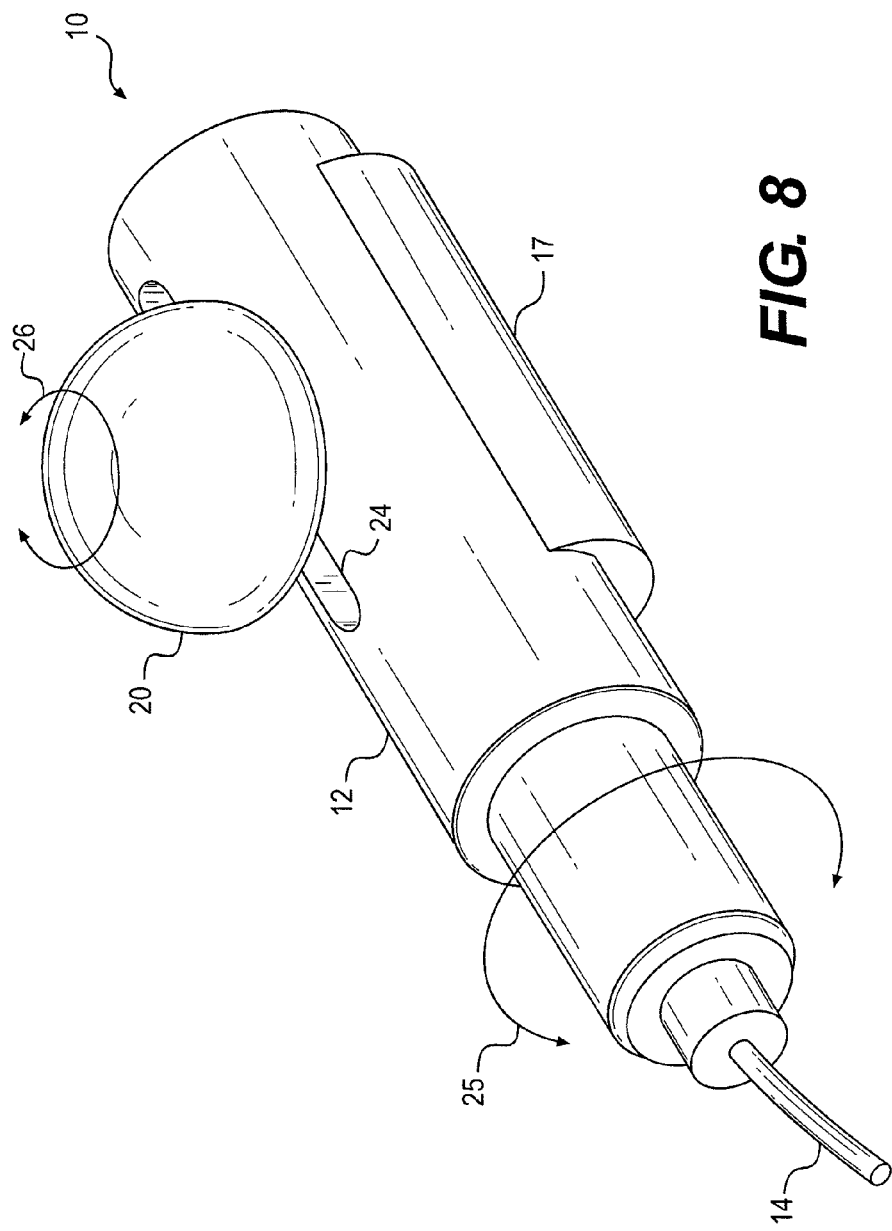
FIG. 8 is an elevated isometric view of a medical device control system in accordance with one embodiment of the present invention.

FIG. 7I illustrates yet another embodiment of trigger mechanism 460 that actuates a tool 304 such as a biopsy forceps with a control wire. In this embodiment, the trigger mechanism is a pneumatic, hydraulic or electromagnetic actuator such as a solenoid, linear motor, etc. that is activated by a switch 462 such as a foot switch. Activation of the trigger selectively tensions or releases a control cable 306 that actuates the tool 304.

Although the described embodiments actuate a tool at the distal end of a steerable medical device, it will be appreciated that the tool may be positioned at other locations on the steerable device.

While embodiments of the invention has been illustrated and described, it will be appreciated that various changes can be made therein without departing from the scope of the invention. For example, additional actuator(s) could be included in the controls to tension/release control cables that terminate at other locations along the length of the medical device. For example, control cables may be secured to a location more proximal than the distal tip in order to provide bending at a more proximal portion of the device. These control cables can be tensioned with a second actuator on the control body. Alternatively, a single actuator can be used to tension more than one set of control cables. The actuator can selectively engage mechanisms to tension different control cables. Brakes or other devices can be used to fix the position of one set of control cables while the control cables from another set are adjusted. With a set of distal control cables and a set of proximal control cables, a tool in the medical device can have up to seven degrees of freedom (up/down, left/right at the distal end, up/down, left/right proximally, forward/backward, rotation about its axis and movement of the tool).

In some embodiments, movement of a medical device in the up/down, left/right direction may be controlled with actuators such as servo motors, hydraulic, pneumatic actuators disposed in a housing that is movable along and rotatable over a fixed rail in order to adjust the distal/proximal movement of a medical device as well as rotation of a device.

In another embodiment, instead of using clamps to secure the control to a rail, the control 10 can be placed in a cradle 17 to allow the control 10 to be rotated about its own longitudinal axis. Alternatively, the clamps that hold the control can be designed with slidable connections or the like to allow the control to rotate about its longitudinal axis. If allowed to rotate, there may be less translation error compared with the embodiments of the invention wherein the control is rotated about the rail that control the longitudinal distal and proximal movement of the medical device.

The embodiments of the invention in which an exclusive property or privilege is claimed are defined as follows:

1. A control for selectively orienting a medical device of the type having control cables configured to actuate a distal tip of the medical device in one or more of an up/down direction and a left/right direction, comprising:
   a body;
   an actuator coupled to the body, wherein the actuator is configured to move independently in at least two directions relative to the body;
   a first pair of control cables mechanically coupled to the actuator and configured to move when the actuator is moved in a first direction;
   a second pair of control cables mechanically coupled to the actuator and configured to move when the actuator is moved in a second direction;
   wherein at least one of the first or second pair of control cables has an inner cable and an outer sheath arranged such that one end of the inner cable and outer sheath move with respect to one another when the actuator is moved in one of said two directions and do not move with respect to each other when the actuator is moved in the other of said at least two directions; and
   a trigger configured to actuate an instrument located at the distal tip of the medical device for performing a procedure on a patient, wherein the trigger is located on the actuator.

2. The control of claim 1, further comprising:
   a rail mounted to a fixed surface with respect to a patient along which the control is moveable to advance or retract the medical device.

3. The control of claim 2, further comprising at least one clamp configured to permit rotation of the body about a longitudinal axis of the rail.

4. The control system of claim 2, further comprising a cradle configured to receive the control, wherein the cradle is configured to permit rotation of the body about a longitudinal axis of the rail.

5. The control of claim 1, wherein the trigger actuates a trigger cable having an inner cable configured to move relative to an outer sheath.

6. The control of claim 1, wherein the trigger actuates a trigger cable that includes a coupler for attachment to a corresponding trigger cable at least partially located within the instrument.

7. The control of claim 6, wherein the coupler includes a spring loaded pin having a receiving notch configured to receive an end of the corresponding trigger cable.

8. The control of claim 1, wherein at least one of the first pair of control cables and the second pair of control cables are located within the body.

9. The control of claim 1, wherein the medical device includes a catheter having a lumen configured to receive the instrument.

10. The control of claim 1, wherein at least one of the first or second pair of control cables includes a coupler for attachment to a corresponding control cable.

11. A method of performing a minimally invasive procedure on a patient with a medical device having a distal tip by:
   delivering the distal tip of the medical device to an internal location within the patient; and
   selectively controlling the orientation of the distal tip of the medical device with a proximally located control that comprises:
      a body;
      an actuator coupled to the body, wherein the actuator is configured to move independently in at least two directions relative to the body;
      a first control cable mechanically coupled to the actuator and configured to move when the actuator is moved in a first direction;
      a second control cable mechanically coupled to the actuator and configured to move when the actuator is moved in a second direction; and
      a trigger moveably coupled to the actuator;
   selectively moving the actuator in the first direction to move the distal tip of the medical device in an up/down direction;
   selectively moving the actuator in the second direction to move the distal tip of the medical device in a left/right direction, wherein movement in the up/down direction is decoupled from movement in the left/right direction; and
   moving the trigger relative to the actuator to actuate an instrument located at the distal tip of the medical device.

12. The method of claim 11, further including moving a distal end of the instrument longitudinally relative to the distal tip of the medical device.

13. The method of claim 11, further including decoupling the control from the medical device.

14. A control system for selectively orienting a medical device, comprising:
a rigid rail having a longitudinal axis;
a clamp configured to move along the longitudinal axis of the rail;
a control fixedly secured to the clamp, wherein the control is configured to move along the longitudinal axis of the rail, the control including:
a body;
an actuator including a handle coupled to a shaft having a longitudinal axis, wherein the shaft is pivotally coupled to the body to permit tilting of the handle with respect to the body, and the shaft is rotationally coupled to the body to permit rotation about the longitudinal axis of the shaft with respect to the body;
wherein the shaft is mechanically coupled to at least two pairs of control cables that are moveable to control the orientation of a distal end of the medical device such that tilting of the handle causes the distal end of the medical device to move in a first plane and rotation of the handle causes the distal end of the medical device to move in a second plane that is different to the first plane; and
a trigger moveably coupled to the actuator and configured to actuate an instrument located at the distal end of the medical device.

15. The control system of claim 14, wherein the shaft is coupled to the body with a trunnion.

16. The control system of claim 15, wherein the shaft is coupled to a cable stop that moves with the shaft and the at least two pairs of control cables include two or more bowden cables coupled to the cable stop.

17. The control system of claim 14, wherein the trigger is located on the handle.

18. The control system of claim 17, wherein the handle is manipulatable by a hand of a user and the trigger is separately manipulatable by a digit of the hand.

19. The control system of claim 14, wherein the handle is elongate and has an elongate axis and the shaft has a first end and a longitudinal axis, further wherein the longitudinal axis of the shaft is positioned generally perpendicular to the elongate axis of the handle, and the first end of the shaft is connected to the handle.

20. The control system of claim 19, wherein the body has a longitudinal axis, and the longitudinal axis of the body is positioned generally perpendicular to the longitudinal axis of the shaft.

* * * * *